(12) United States Patent
Molloy et al.

(10) Patent No.: US 8,742,334 B2
(45) Date of Patent: Jun. 3, 2014

(54) SPINNING CELL DEVICE FOR FAST STANDARDIZATION IN LASER ABLATION INDUCTIVELY COUPLED PLASMA SPECTROMETRY

(71) Applicants: John L. Molloy, Gaithersburg, MD (US); Naomi Bier, Houston, TX (US); Fanny Claverie, Pau (FR); Julien F. C. Malherbe, Pau (FR)

(72) Inventors: John L. Molloy, Gaithersburg, MD (US); Naomi Bier, Houston, TX (US); Fanny Claverie, Pau (FR); Julien F. C. Malherbe, Pau (FR)

(73) Assignee: The United States of America, as represented by the Secretary of Commerce, the National Institute of Standards and Technology, Washington, DC (US)

( * ) Notice: Subject to any disclaimer, the term of this patent is extended or adjusted under 35 U.S.C. 154(b) by 0 days.

(21) Appl. No.: 13/867,012

(22) Filed: Apr. 19, 2013

(65) Prior Publication Data

US 2014/0070085 A1    Mar. 13, 2014

Related U.S. Application Data

(60) Provisional application No. 61/669,151, filed on Jul. 9, 2012.

(51) Int. Cl.
*B01D 59/44* (2006.01)
*H01J 49/00* (2006.01)
*G01J 3/30* (2006.01)
*G02B 21/26* (2006.01)

(52) U.S. Cl.
USPC ........... 250/282; 250/425; 250/281; 250/288; 356/318; 356/302; 356/303; 356/326; 359/394; 359/398; 204/157.41

(58) Field of Classification Search
USPC ............ 250/281, 282, 288, 299, 423 R, 424, 250/425, 526; 356/302, 303, 305, 311, 317, 356/318, 326; 219/121.63, 121.64, 121.68; 359/394, 398, 410, 896; 204/157.41
See application file for complete search history.

(56) References Cited

U.S. PATENT DOCUMENTS

| | | | |
|---|---|---|---|
| 5,231,047 A | 7/1993 | Ovshinsky et al. | |
| 6,873,419 B2 * | 3/2005 | Detalle et al. | 356/479 |
| 8,207,494 B2 | 6/2012 | Hieftje et al. | |
| 8,274,735 B2 * | 9/2012 | Fry et al. | 359/393 |

(Continued)

OTHER PUBLICATIONS

U.S. Appl. No. 10/525,433, filed May 25, 2006, Hayashizaki, et al.

(Continued)

*Primary Examiner* — Bernard E Souw
(74) *Attorney, Agent, or Firm* — Absolute Technology Law Group, LLC (57) ABSTRACT

A spinning cell device is described for fast and convenient standardization and analysis of constituents and isotopes in solid samples by laser ablation inductively coupled plasma (LA-ICP) spectrometry. The method and apparatus for performing the method require the sample under test and a standard to be spun during ablation allowing the quasi-simultaneous ablation of both materials. The aerosols resulting from the ablation of sample and standard are mixed in the ablation cell allowing quantification of the ablated metals by the method of standard addition or isotope dilution. The relative proportion of standard verses sample ablated can be changed by altering the trajectory of the laser beam. The ablated aerosol is swept into an inductively coupled plasma by a carrier gas and analyzed by mass spectrometry.

18 Claims, 8 Drawing Sheets

(56) References Cited

U.S. PATENT DOCUMENTS

| | | | |
|---|---|---|---|
| 8,317,983 | B1 | 11/2012 | Holloway et al. |
| 8,319,964 | B2 | 11/2012 | Hahn |
| 8,586,943 | B2* | 11/2013 | Verbeck et al. ............... 250/429 |
| 2006/0108538 | A1* | 5/2006 | Hayashizaki et al. ..... 250/423 P |
| 2009/0073586 | A1* | 3/2009 | Fry et al. ....................... 359/839 |
| 2012/0000893 | A1* | 1/2012 | Broude et al. ........... 219/121.69 |

OTHER PUBLICATIONS

U.S. Appl. No. 13/112,575, filed Jan. 5, 2012, Broude, Sergey V et al.

U.S. Appl. No. 12/283,698, filed Mar. 19, 2009, Fry, Robert C et al.

* cited by examiner

SPINNING CELL DEVICE FOR FAST STANDARDIZATION IN LASER ABLATION INDUCTIVELY COUPLED PLASMA SPECTROMETRY

CROSS-REFERENCE TO RELATED APPLICATIONS

This application claims priority to U.S. Provisional Application No. 61/669,151 filed on Jul. 9, 2012.

STATEMENT OF GOVERNMENT INTEREST

The invention described herein was made by employees of the United States Government and may be manufactured and used by or for the Government of the United States of America for governmental purposes without the payment of any royalties thereon or therefor.

FIELD OF INVENTION

The present invention relates to the field of Laser Ablation Inductively Coupled Plasma (LA-ICP) spectrometry, and more specifically to a spinning cell device for LA-ICP spectrometry which makes possible a fast and convenient method for standardizing and analyzing samples using.

TERMS OF ART

As used herein the term "ablation" refers to the process of causing a solid material to be vaporized, sublimed, formed into a plasma, made into an aerosol or broken into fine particles and thrown away from the surface of the solid by the action of a laser beam.

As used herein, the term "ablative material" means a material capable of being transformed from a solid to a gas when placed in contact with a labor beam.

As used herein the term "ablation products" refers to a material that results from ablation after a laser beam has been applied to an ablative material, which includes but is not limited to analytes.

As used herein the term "analyte" refers to the chemical constituent of interest in a chemical analysis. An analyte may be an abalation product As used herein the term "fluidly connected" refers to the structural joining or adjacent positioning of two or more enclosed chambers in a manner which allows transfer of as a gas or liquid from one chamber to another.

As used herein the term "inert gas" refers to a gas which will not react with either the materials generated in a laser ablation process or the materials making up the ablation cell or the transport tubing. As used herein the term "matrix" refers to the components of a sample under test other than the analyte(s) of interest.

As used herein the term "multi-element standard" refers to a standard which includes many elements of known quantity.

As used herein the term "sample submitted for analysis" refers to a material intended for analysis by an analytical technique such as LA-ICP-MS in the form that it is first received by the lab and before any preparation has been made for the analysis.

As used herein the term "sample under test" refers to a material submitted for analysis that has undergone processes which make it appropriate for instrumental analysis such as dissolution in a solvent, incorporation in a glass matrix, or mixing with a material of known composition.

As used herein the term "revolvable sample receptacle" refers to a cell holder which is configured to rotate or spin under the application of a torque supplied manually, by a motor, or by another energy source.

BACKGROUND

Mass spectrometry is an analytical technique used for identifying the composition of a substance based on the mass of the substance or of constituent atoms or molecular fragments into which it may be broken. It is particularly valuable because it frequently requires little information about the sample submitted for analysis to obtain useful results. For example in the qualitative analysis of a sample under test containing metal atoms, the constituent metal atoms and isotopes can be identified by their atomic mass.

In a mass spectrometry experiment it is normally necessary to make the sample under test available to the inductively coupled plasma ionization system as a vapor or aerosol then ionize the material so that its mass may be analyzed by accelerating the ions using an electric or combination of electric and magnetic fields. The mass of the constituent parts is determined from the ratio of the mass of the particle to its charge. The substance or chemical constituent that is of interest in an analytical procedure is referred to as an analyte. The material to be analyzed in the form obtained initially by the lab is referred to as the "sample submitted for analysis". The material to be analyzed in a form ready for analysis is referred to as the sample under test. Frequently the results of the analytical procedures on a first sample under test are compared to the results of those same procedures on a second sample of known concentration. This second sample of known concentration is referred to as a standard. Standards may be in the form of separate samples under test or they may be added to the sample as submitted before analysis in which case they are known as internal standards.

Inductively coupled plasma (ICP) is a technique for ionizing a vaporized sample. It is used in the art for elemental determinations by mass spectrometry. ICP has been used as an ionization technique with a variety of analytical techniques such as atomic emission spectroscopy. When the ionization method of ICP is used as the ionization method for a subsequent analysis by mass spectrometry the technique is referred to as inductively coupled plasma mass spectrometry (ICP-MS). ICP-MS typically requires introduction of a sample into the plasma discharge as an aerosol. The plasma discharge converts the aerosol into elemental ions which can be analyzed by the mass spectrometer. Sometimes an additive is introduced after the aerosol is formed to insure the aerosol is completely ionized by the inductively coupled plasma. In the exemplary embodiment shown this is a dilute solution of a highly oxidizing acid such as 2% nitric acid.

Sometimes a technique known as isotope dilution is used in connection with ICP-MS. Isotope dilution ICP-MS is based on the addition of a known amount of an enriched isotope (called the "spike") to a sample. After equilibration of the spike isotopes with the natural isotopes in the sample, mass spectrometry is used to measure the altered isotopic ratio(s). The concentration is directly derived from this ratio.

Laser ablation (LA) is a technique known in the art used to make an aerosol that can be transported by an inert carrier gas such as helium into the plasma discharge. Laser ablation has been used with liquid and solid samples and compliments the ICP ionization technique. Normally a laser is focused on a sample under test within an ablation chamber. The light from the laser heats the sample until it ablates, and the resulting aerosol is swept into the inductively coupled plasma (ICP) chamber by an inert carrier gas such as helium. The results of the laser ablation process are highly dependent on the sample however. Different samples under test absorb different amounts of the laser light, and so for some samples only a surface layer is removed, and for other samples the ablation penetrates more deeply into the sample.

Laser ablation inductively coupled plasma mass spectrometry (LA-ICP-MS) is considered one of the most powerful techniques for identifying trace elements in sold materials. LA-ICP-MS uses a laser to ablate or vaporize a portion of the sample on or near the surface the laser is focused on. LA-ICP-MS is used for analysis of solid samples in geological, archeological, environmental and biological studies. LA-ICP-MS is fast, sensitive and able to probe micro-scale features.

However, there are limitations known in the art with respect to LS-ICP-MS in that detection capabilities will vary with the sample matrix, which may affect the degree of ionization that will occur in the plasma or allow the formation of species that may interfere with the analyte determination.

Another problem known in the art with LA-ICP-MS is the susceptibility of the process to errors caused by contamination, matrix effects and inter-element fractionation. Each of these phenomena compromise attempts at standardization and makes accurate quantification hard to achieve. Many researchers have developed complicated strategies to overcome these obstacles such as the use custom matrix matched standards, liquid ablation, dual introduction (sample+standard), and isotope dilution. All these methods are time consuming, and many are difficult and costly as well. Custom matrix matched standards involves making up several samples continuing standards in the matrix of the sample. In this technique a different set of standards or a different matrix needs to be used for each sample or sample type analyzed. This process of preparing a different standard for every analysis is cumbersome, tedious, and expensive. Liquid ablation has the same issues as other custom standard method and additionally requires special sample handling to minimize splashing and other effects of the ablation process. Isotope dilution as taught in the art requires the addition of isotope enriched standards for every element suspected of being present in the sample.

The method of standard addition is used in instrumental analysis to determine concentration of a substance in an unknown sample by comparison to a set of samples of known concentration, similar to using a calibration curve. However, because the results of LA-ICP-MS are known to be sensitive to matrix effects, contamination, and inter-element fractionation, it is appreciated in the art that the method requires a time consuming process of preparing mixtures of sample and standards. The method of standard addition can be implemented by preparing several samples for analysis containing the same amount of unknown, but different amounts of standard. The idea of this procedure is that the total concentration of the analyte is the combination of the unknown and the standard, and that the total concentration in the set varies linearly. If the signal response is linear in this concentration range, then the relative amounts of the constituents in the sample are solved for using equations containing the known amounts of the standard and the relative amounts of the constituents in the standard.

However, in the case of most LA-ICP techniques including LA-ICP-MS the sample preparation usually includes a tedious process of spiking, homogenizing, drying and pelletizing steps that need to be repeated for each additions of a single sample. Nevertheless, this method has been successfully used for the analysis of viscous crude oil, zircons fused in glass and hardly digestible samples prepared with a gluing technique.

An online solution based addition developed for laser ablation microprobe ICP-MS and then for LA-ICP-MS analysis and been shown to minimize the time consuming nature of standard additions when used with laser ablation. This method consists of performing the addition by mixing the ablated sample with a nebulized elemental solution using a Y connection. A similar approach involves mixing the aerosol coming from an ultrasonic nebulizer with the ablated particles directly inside the ablation cell. Even though these techniques have shown promising results they require researchers to identify at least one element in advance of the analysis and prepare an appropriate standard solution for that element, and/or factor in the ablation rate for each element. The ablation rate may or may not be known with the appropriate accuracy to make this technique possible.

It is desirable to have the ability to add a test component to a sample to calibrate the testing method, account for impurities, and eliminate matrix effects. However, doing so in conjunction with laser ablation involves a time-consuming sample preparation process for solid sample types. Various sample preparation methods known in the art as spiking, homogenizing, drying and pelletizing steps need to be repeated for each additions of a single sample. These methods have been successfully used for the analysis of viscous crude oil; zircons fused in glass and hardly digestible samples prepared with a gluing technique, but are cumbersome, tedious, and expensive.

Recently a new approach implying the mixing of two aerosols has been investigated. This technique is based on a system equipped with a galvanometric scanning beam device that allowed the laser to rapidly move with high repositioning precision. Using such a device, the quasi-simultaneous ablation of the sample and an isotopically enriched pellet was realized, thus performing the isotope dilution (ID) directly inside the ablation cell. However, this method requires the use of specialized instrumentation, expensive isotopically-enriched standards, and assumes that the same amount of material has been ablated between the sample and the spike pellet.

It is desirable to have a convenient, inexpensive method for successfully introducing an additive of known composition in the same matrix as the analyte which may be used to implement the methods of standard addition or isotope dilution for LA-ICP-MS. It is further desirable to have material which can serve as standards be reusable over many analyses.

SUMMARY OF THE INVENTION

The present invention is a dual matrix LA-ICP spectroscopic method for performing LA-ICP on a spinning sample cell and an apparatus uniquely adapted to perform all steps of the specific ablation method herein. The apparatus herein is uniquely and specifically configured to perform each step of the method herein without the exclusion or modification of the steps disclosed. The method and apparatus jointly achieve laser ablation inductively coupled plasma (LA-ICP) spectrometry which allows rapid and convenient quantitative analysis and standardization of solid samples.

A dual matrix LA-ICP spectroscopic analysis system is specifically adapted for performing a method of dual matrix LA-ICP. The apparatus is comprised of an ablation chamber which is fluidly connected to an inductively coupled plasma ionization chamber. Both chambers are connected to allow the passage of gasses between them through correspondingly placed apertures.

The ablation chamber housing is adapted for passage of a laser beam. A spinning sample receptacle (which may be a plate, platform or other structure adapted to secure samples through the use of centrifugal force) and variable position of the sample relative to the trajectory of the laser beam. The apparatus method may include optional analyte sensing components, computer analytics, memory storage and processing component and other hardware and software components used for instrumental chemical analysis. The method and apparatus enable the use of the method to increase the efficiency and reduce the cost of performing the method of standard addition by introducing components and steps to performing LA-ICP while a sample under test and standard are spinning.

A spinning cell device is described for fast and convenient standardization and analysis of constituents and isotopes in solid samples by laser ablation inductively coupled plasma (LA-ICP) spectrometry. The method and apparatus for performing the method require the sample under test and a standard to be spun during ablation allowing the quasi-simultaneous ablation of both materials. The aerosols resulting from the ablation of sample and standard are mixed in the ablation cell allowing quantification of the ablated metals by the method of standard additions. The relative proportion of standard verses sample ablated can be changed by altering the path of the laser beam relative to the sample. The ablated aerosol is swept into an inductively coupled plasma ionization chamber by a carrier gas and analyzed.

DETAILED DESCRIPTION OF INVENTION

For the purpose of promoting an understanding of the present invention, references are made in the text to exemplary embodiments of a spinning sample cell device for laser ablation inductively coupled plasma (LA-ICP) spectrometry, only some of which are described herein. It should be understood that no limitations on the scope of the invention are intended by describing these exemplary embodiments. One of ordinary skill in the art will readily appreciate that alternate but functionally equivalent spinning sample cell devices for laser ablation inductively coupled plasma (LA-ICP) spectrometry may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related. For example the term "substantially similar matrix" is one into which a sample under test and a standard may be incorporated. In the method of standard addition efforts are made to make the matrix of a sample under test and a standard so similar that any differences of the matrix does not affect the instrument response.

The invention disclosed herein and the inherent method of its use makes the techniques of LA-ICP spectrometry quantitative while overcoming the cumbersome and time consuming deficiencies of the techniques in the prior art.

Figure 1:
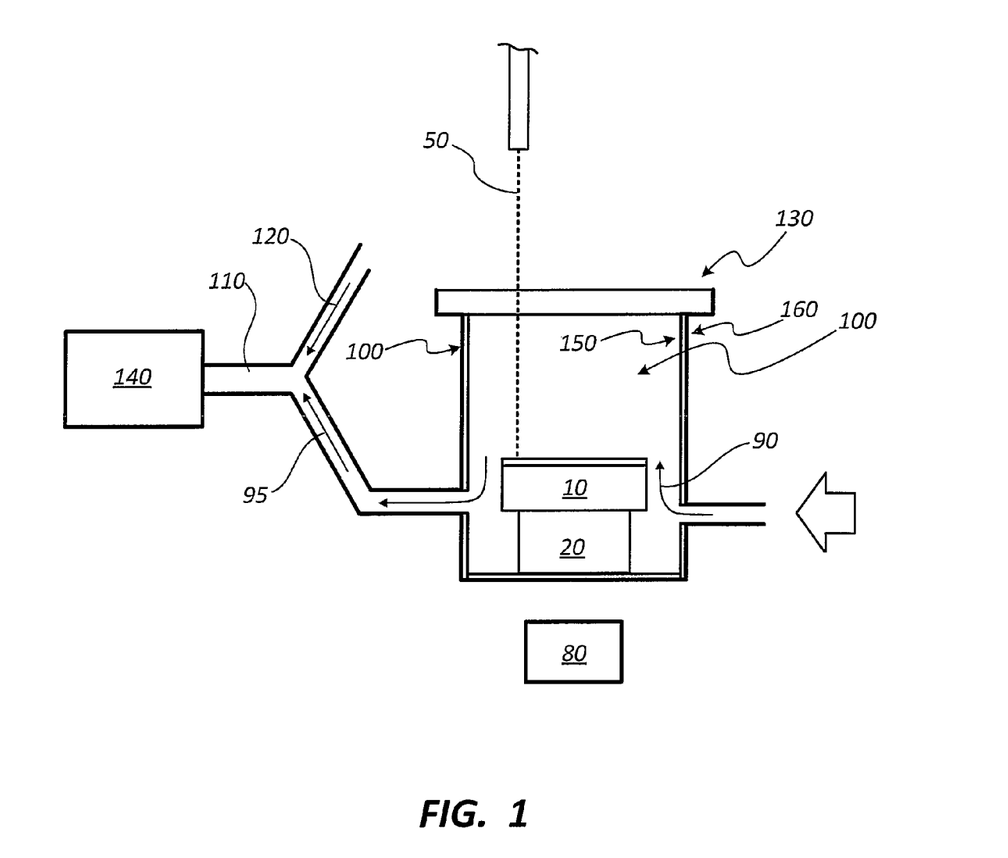
FIG. 1 illustrates an exemplary embodiment of an ablation chamber containing a spinning sample cell for fast standardization and analysis by LA-ICP.

FIG. 1 illustrates a side sectional view of an exemplary embodiment of an ablation chamber containing a spinning sample cell for fast standardization and analysis by LA-ICP spectrometry.

FIG. 1 shows an exemplary embodiment of an ablation chamber 100 with interior walls 150, and exterior walls 160 defining an interior of the ablation chamber 105. FIG. 1 illustrates an exemplary embodiment of a laser beam trajectory 50. FIG. 1 shows an exemplary embodiment of an ablation chamber 100 adapted for passage of a laser beam by a transparent window 130 which allows the beam to pass to the interior of the ablation chamber 105. The exemplary embodiment shown in FIG. 1 illustrates the use of an inert carrier gas 90 which enters the inside of ablation chamber 100 and sweeps out the ablation products so that upon exiting the ablation chamber it is an inert carrier gas with ablated products 95. In the exemplary embodiment the ICP ionization chamber is part of an ICP-MS instrument.

The laser ablation system employed in the exemplary embodiment is a (Photon Machine Analyte 193) pulsed argon fluoride excimer laser configured to produce 4 nanosecond pulses of 193 nm light at a repetition rate of 20 Hz. It should be noted that in the exemplary embodiment illustrated the speed of the motor 80 and the spinning rate of the spinning sample holder 10 is 2000 rpm. Thus in the illustrated exemplary embodiment the spinning sample holder executes about 1.7 revolutions between laser pulses. In the exemplary embodiment shown the laser beam traveling along laser beam trajectory 50 is focused to a spot size of 138 millimeters with a radiative flux of 7 joules/square centimeter. In the exemplary embodiment illustrated the sample moves relative to the laser beam trajectory and mass spectral data is collected for a given sample or mixture of sample and standard. The term "ablation period" refers to the period of time in over which a set of analytical data is continuously collected on a sample or mixture of sample and standard. In the exemplary embodiment illustrated many laser pulses are emitted by the laser over a given ablation period each producing ablation products from the location that the laser contacts the sample or the standard. In the exemplary embodiment shown the locations of the ablations for a given ablation period produce a circular pattern on the sample or sample and standard referred to as an ablation track.

In the exemplary embodiment illustrated the inert carrier gas 90 is helium and the flow rate of the inert carrier gas 90 and consequently the inert carrier gas with ablated products 95 is 550 cubic centimeters per minute. It should be emphasized that an important aspect of the exemplary embodiment of the spinning cell device as illustrated in FIG. 1 is that allows the mixing of sample and standard in the ablation chamber In the illustrated exemplary embodiment shown in FIG. 1 the inert carrier gas with ablated products 95 is mixed with an exemplary embodiment of a post-ablation additive 120 used to insure the ablated products are completely ionized by the inductively coupled plasma. In the exemplary embodiment shown the post-ablation additive 120 is a nebulized 2% nitric acid solution. FIG. 1 shows the post-ablation additive 120 is mixed with inert carrier gas with ablated products 95 in a Y-connection 110 before entering the ICP ionization chamber 140. The optimization of the coupling in the exemplary embodiment illustrated is performed by determining the ICP-MS detector dead-time and adjusting the flow rates in the Y connection with a 2 nanogram/gram multi-elemental solution in place of the inert carrier gas with ablated products 95 and monitoring the MS-ICP signal so that maximum sensitivity is achieved with low oxide level (less than 3%).

The ICP ionization chamber 140 in the exemplary embodiment illustrated in FIG. 1 is part of an ICPMS PQ3 (Thermo Elemental) mass spectrometer having nickel cones material operated under wet plasma configuration with a dwell time of 20 milliseconds. In the exemplary embodiment shown the ICP ionization chamber uses its own supply of Argon with flow rates of plasma gas 13.6 liters/minute, auxiliary gas 0.88 liters/minute, and carrier gas of 0.85 liters/minute for the operation of the chamber.

The exemplary embodiment of an ICP ionization chamber illustrated in FIG. 1 shows an exemplary embodiment of a post-ablation additive used to insure the ablated aerosol is completely ionized by the inductively coupled plasma.

FIG. 1 illustrates an exemplary embodiment of motor 80 which in the present embodiment is a brushless flat DC-Micromotor (Series 260T012B) commercially available from Faulhaber (Schonaich, Germany) and used to cause the spinning platform 20, and the spinning sample holder 10 to spin during the ablation period. The "Faulhaber Motion Manager" software is used to operate the motor 80 with controlled revs (up to 7000 rpm).

Figure 2:
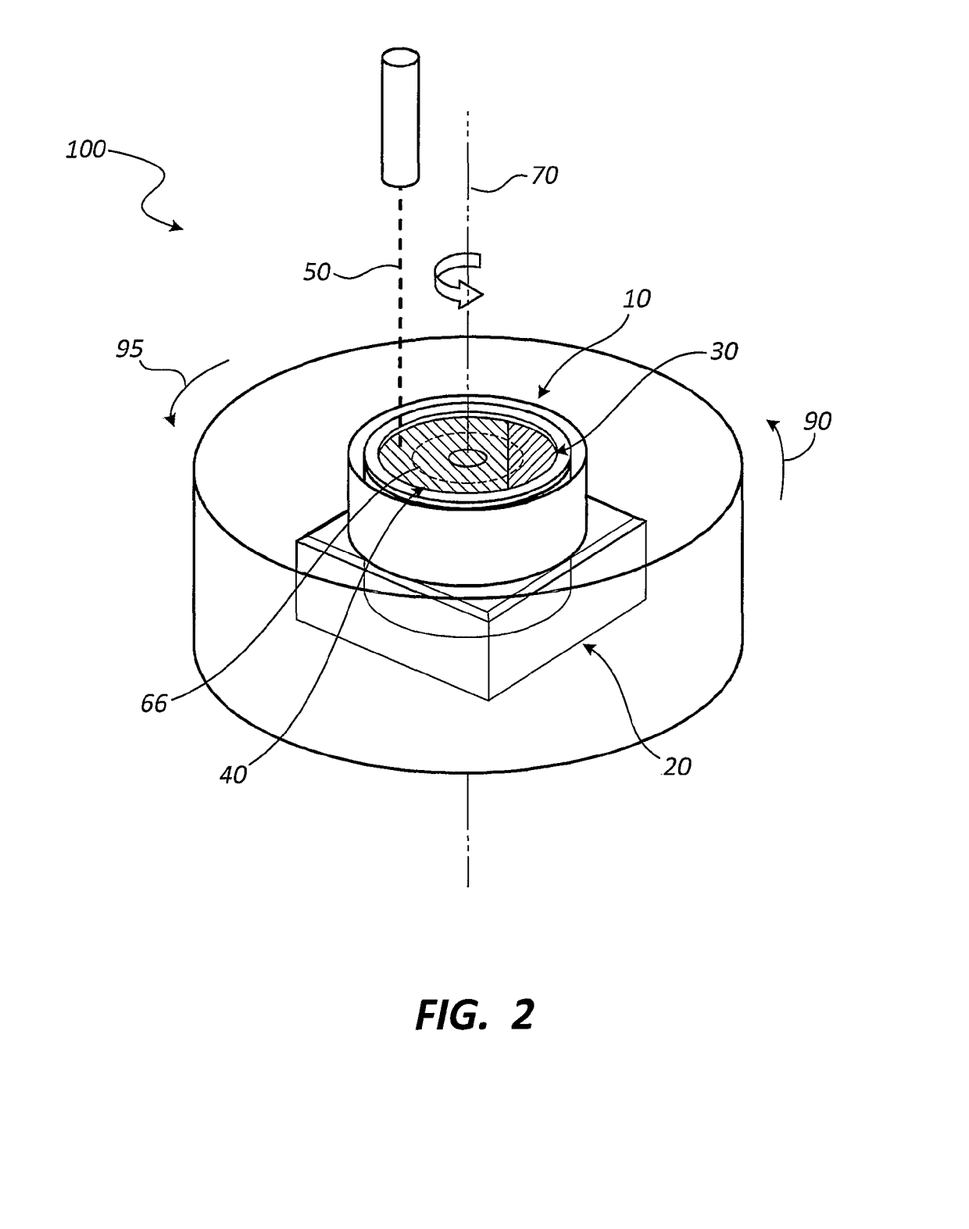
FIG. 2 illustrates an exemplary embodiment of a spinning sample cell for fast standardization and analysis by LA-ICP.

FIG. 2 illustrates an exemplary embodiment of a spinning sample cell for fast standardization and analysis by LA-ICP-MS. The cell permits standardization and analysis of LA-ICP-MS samples in a convenient and reproducible manner which overcomes the deficiencies of cumbersome and tedious approaches in the prior art. FIG. 2 illustrates the inside of an ablation chamber 100 also shown in FIG. 1. FIG. 2 illustrates an exemplary embodiment of a spinning sample holder 10 which holds a sample spiked with natural gadolinium (Gd) 30. The element gadolinium (atomic symbol Gd) is rare and generally is not expected to be in the sample submitted for analysis. By adding a known amount of this material to the sample matrix the natural abundances of the gadolinium isotopes will identify the gadolinium added to the sample in the subsequent mass spectrometric analysis. FIG. 2 also shows an exemplary embodiment of a multi-element standard with enriched Gd (157). The gadolinium enriched in isotope 157 identifies the gadolinium coming from the multi-element standard in the subsequent mass spectral analysis. It is an important aspect of the present invention that ablation products from the standard are mixed with ablation products of the sample in the ablation chamber before being swept in the present embodiment by the inert carrier gas 90 as it becomes inert carrier gas with ablated products 95 and carried into the ICP-MS.

FIG. 2 illustrates how the sample spiked with natural Gd and the multi-element standard with enriched Gd (157) can be simultaneously ablated. FIG. 2 shows laser beam trajectory 50 as it makes an exemplary ablation track over a given ablation period yielding sample and a large amount of standard 66 as the spinning sample holder 10 spins around the motor axis 70. In the present embodiment the sample holder 10 rotates at 2000 rpm but in the present embodiment the laser beam consists of pulses of 4 nanoseconds focused to a spot size of 138 micrometers with a repetition rate of 20 Hz. In the present embodiment the laser light is produced from an argon fluoride excimer laser with a wavelength of 193 nanometers and is able to ablate a small spot on either the sample spiked with natural Gd 30 or the multi-element standard with enriched Gd (157) 20 times a second. Thus material from spots on both the multi-element standard with enriched Gd(157) 40, and from the sample spiked with natural Gd 30 are both ablated and mixed in the ablation chamber at once. The isotopic ratios of the gadolinium detected in the mass spectrometer identify the relative amounts of the sample spiked with natural Gd 30 or the multi-element standard with enriched Gd(157) 40.

Figure 3:
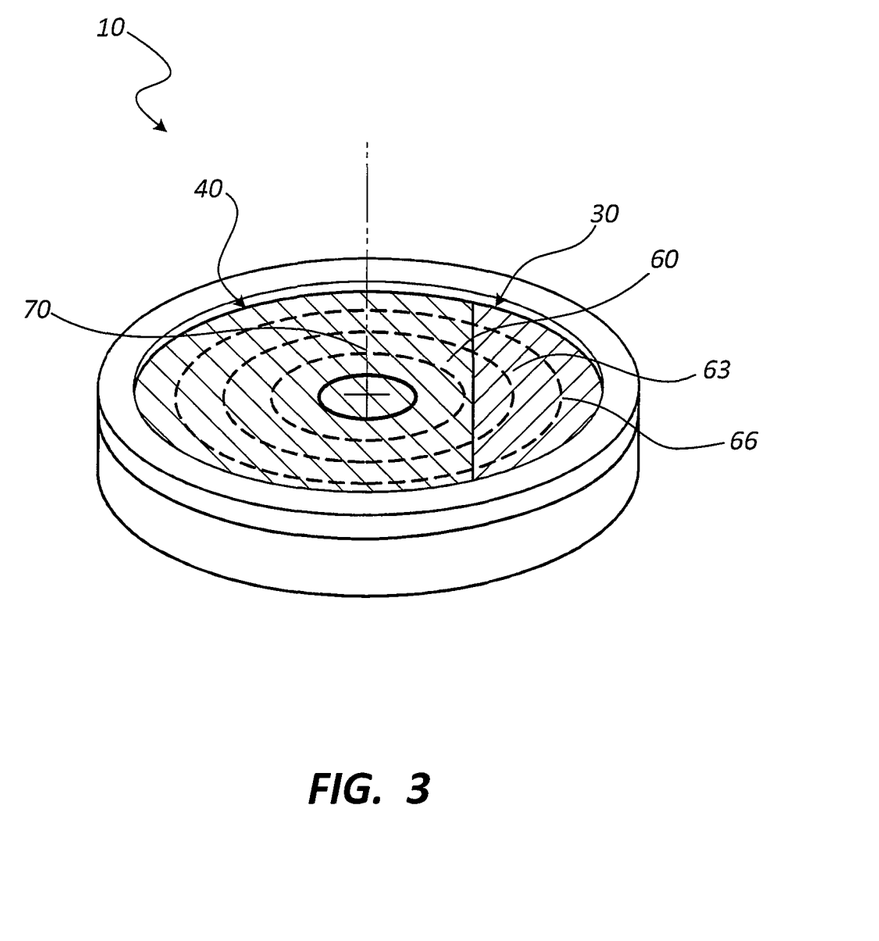
FIG. 3 illustrates the placement of sample and standard within an exemplary spinning cell for fast standardization and analysis by LA-ICP.

FIG. 3 illustrates an exemplary embodiment showing a placement of sample and standard in the spinning sample holder 10. FIG. 3 shows the motor axis 70, the multi-element standard with enriched Gd (157) 40, the sample spiked with natural Gd, 30. FIG. 3 illustrates how it is possible to vary the relative amount of the standard that is ablated with the sample by changing the position of the laser so that it makes for example an ablation track yielding sample only 60, an ablation track yielding sample+a small amount of standard 63, or an ablation track yielding sample+a large amount of standard 66. Such variation is an important aspect of the method of standard addition, and allows the determination of the relative amount of any element that is present in both the sample and the standard. In the present embodiment the multi-element standard with enriched Gd (157) contains metal atoms of nickel, copper, zinc, strontium, barium, and lead, but could contain any other elements likely to be found in the samples that might be analyzed. In the exemplary embodiment shown the sample glass is cast into the same mold as the standard glass, but the multi-element standard glass is cut in two with a diamond saw. A single half multi-element standard glass is placed on the sample in the spinning sample holder 10 in order to ablate both sample and multi-element standard during the rotation or sample alone. The multi-element standard glass is shifted 1.5 mm away from the motor axis 70 so that when a laser beam trajectory 50 less than 1.5 mm from the motor axis 50 is used it will produce an ablation track yielding sample only 60. During a typical analysis the laser beam trajectory 50 is changed so different mixtures of sample and standard can be analyzed.

The method of isotope dilution can also be used by a method similar to that described in the previous paragraph. The difference is that the sizes of sample (60) and standard (63) are the same, and the standard is not spiked with a higher level of analyte, but rather with an enriched isotope.

Six standard reference materials (SRM)s are used to demonstrate the suitability of the exemplary embodiment and the application of the standard addition technique using a spinning sample cell for LA-ICP-MS. These materials are treated as "samples as submitted" for the purposes of demonstrating the exemplary embodiment and their elemental composition is determined using the exemplary embodiment and then compared to their known composition. SRM 1944 (New York/New Jersey waterway sediment), SRM 2586 (trace elements in soil containing lead from paint), SRM 2702 (inorganics in marine sediment), SRM 2711a (Montana H soil), SRM 688 (basalt rock) and SRM 612 (Trace elements in glass) from NIST (National Institute of Standards and Technology, Gaithersburg USA). Additionally, the Allende meteorite (USNM 3529 Split 5 pos. 20) under powdered form graciously provided by the Smithsonian institution (Washington D.C., USA) and is used to demonstrate the exemplary embodiment illustrated.

Figure 4:
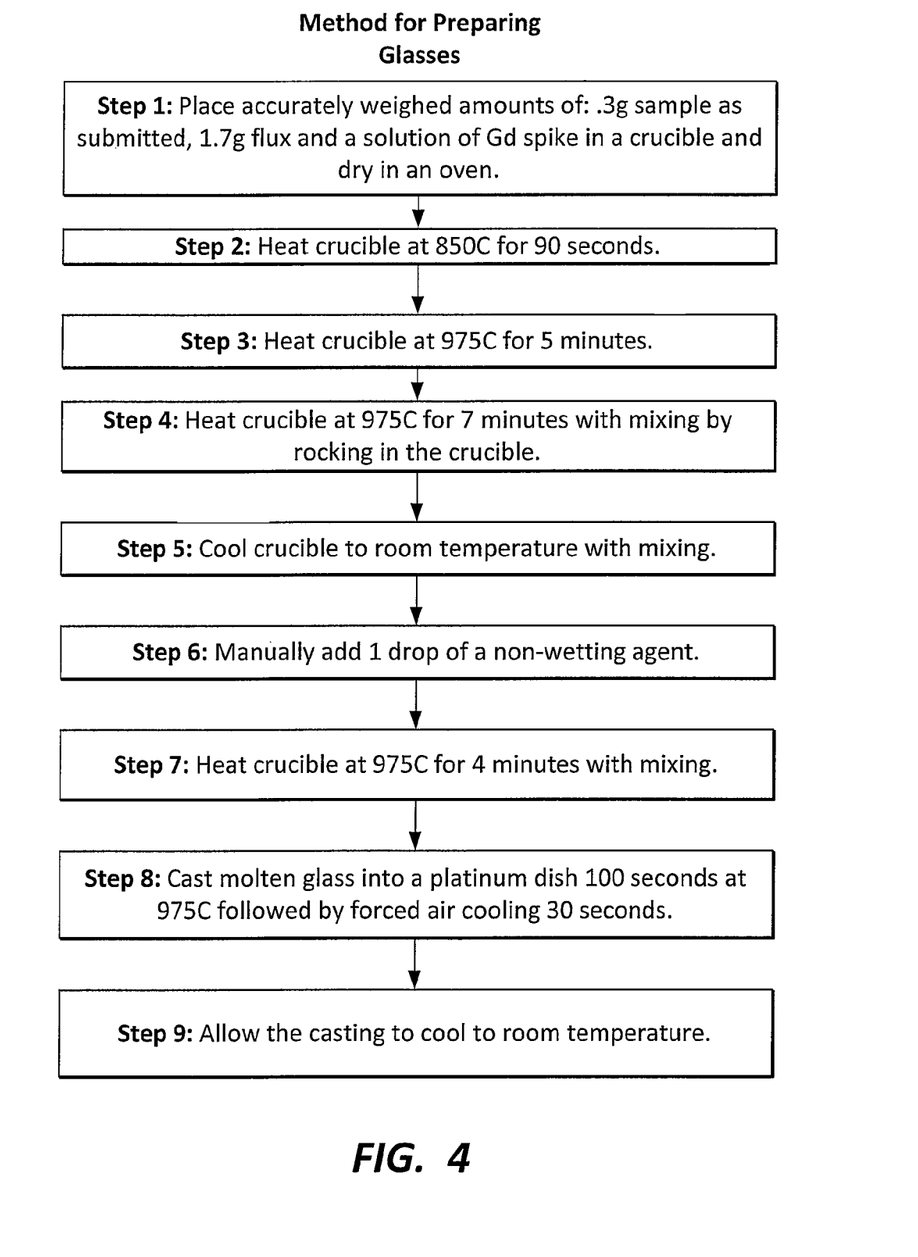
FIG. 4 illustrates a flowchart of an exemplary method for preparing both sample and standards for analysis with the spinning cell for LA-ICP.

FIG. 4 is a flow chart illustrating an exemplary embodiment of a method for preparing both sample and standards for analysis with the spinning cell for LA-ICP-MS. In the exemplary method each sample is spiked with natural Gd, and the standards prepared are multi-element standards with enriched Gd(157).

The method in the illustrated embodiment eliminates the effect of variations particle size and composition within a given sample submitted for analysis. The multi-element standard with enriched Gd(157) and all samples spiked with natural Gd used in the LA-ICP-MS studies of the illustrated exemplary embodiment are made into glasses by this method. The method is generally known in the art as the borate fusion method and comprises in the exemplary embodiment mixing an accurately weighed amount of SRM (0.3 g) with an accurately weighed amount of flux (1.7 g of lithium borate of 67 weight % $Li_2B_4O_7$ including 33 weight % $LiBO_2$) commercially available from Spex, New Jersey USA) in a 30 mL capacity platinum crucible. These 2 g mixtures of material are then spiked with a known amount of a solution containing natural Gd, dried in an oven, and fused using a Perl 'x31 induction-heated machine (PANalytical, Almelo, The Netherlands). The fusion program shown in FIG. 4 consists of the following steps:

Step 1: Place an accurately weighed amounts of: 0.3 g sample as submitted, 1.7 g flux, and a solution of Gd spike in a crucible and dry in an oven.

Step 2: Heat crucible at 850 C for 90 seconds.

Step 3: Heat the sample to 975 C for 5 minutes.

Step 4: Heating the sample to for 7 min with mixing by rocking the crucible.

Step 5: Cool to room temperature (with mixing).

Step 6: Manually add one drop of a non-wetting agent, which in the exemplary embodiment is a 20 weight % solution of lithium iodide.

Step 7: Heat to 975° C. for 4 min (with mixing).

Step 8: Cast into a platinum dish 100 seconds at 975C.

Step 9: Allow the casting to cool to room temperature.

The standard reference materials SRM series 3000 spectrochemical solutions available from the National Institute of Standards and Technology (NIST) are used to prepare two multi-element standards with enriched Gd(157). The standards used in the exemplary embodiment are glasses containing many elements that may be expected in samples to be analyzed by LA-ICP-MS over a period of time. These multi-element standards are glasses that are spiked with an accurately weighed amount of a n isotopically enriched Gd(157) solution whereas each sample for analysis is spiked with a solution of natural Gd. The Gadolinium used to spike the samples is the material: SRM NIST 3118a available from NIST. Spike solution of Gd(157) is prepared by dissolution in nitric acid of an accurately weighed amount of enriched gadolinium oxide ($Gd_2O_3$. Gd(157)=88.63 weight %) purchased from Trace sciences international (Richmond Hill, ON Canada). This enriched Gd(157) solution is diluted and analyzed by ICP-MS to determine its isotopic abundance and by ID-ICPMS for the elemental concentration.

Two multi-element glasses (one of 250 mg/kg, and the other of 500 mg/kg) are prepared by spiking an accurately weighed amount of flux (2 g) with a multi-elemental solution of Pb, Sr, Ba, Ni, Cu, Zn and an isotopically enriched solution of Gd(157). The mixture is then dried in an oven and fused using the method same protocol as described above. Table 1 shows the concentration of both multi-element glasses determined by ID-ICPMS after dissolution in nitric acid and the isotopic abundances obtained for Gd. Finally each lithium borate glass bead is cut in half using a diamond saw. It should be emphasized that the multi-element glasses of the illustrated embodiment may be reused for another sample after polishing for example with an emery cloth. This means that preparation of the standard is considerably more convenient than techniques in the prior art.

TABLE 1

Concentrations of Multi-element Standards

| | 250 mg/Kg glass Concentration (mg/Kg) | 500 mg/Kg glass Concentration (mg/Kg) |
|---|---|---|
| Ni | 263.5 ± 26.2 | 539 ± 40 |
| Cu | 252.2 ± 5.3 | 482.8 ± 18.7 |
| Zn | 298.8 ± 11.2 | 506 ± 20 |
| Sr | 259.9 ± 0.9 | 504.2 ± 23.5 |
| Ba | 253.8 ± 6.8 | 492.4 ± 15.6 |
| Pb | 257.3 ± 1.6 | 497.9 ± 24.8 |
| Gd | 159.4 ± 1.2 | 155.6 ± 8.9 |

Gadolinium is chosen because it is not present in the soils to be analyzed and because its isotopes are not prone to interferences due to elements in the samples matrices. The Gadolinium additions (natural and isotopically enriched), allow accessing the amount of material ablated from the sample (SRM) and the multi-elemental glass using the method of isotope dilution. Two problems known in the art of laser ablation, elemental and isotopic fractionations do not have a significant impact in the exemplary method because both the standard and the sample are in similar matrices of lithium borate (flux) since both are made by the fusion process illustrated in FIG. 4.

The laser ablation system employed in the exemplary embodiment is a pulsed argon fluoride excimer laser configured to produce 4 nanosecond pulses of 193 nm light at a repetition rate of 20 Hz. It should be noted that in the exemplary embodiment illustrated the speed of the motor 80 and the spinning rate of the spinning sample holder 10 is 2000 rpm. Thus in the illustrated exemplary embodiment the spinning sample holder executes about 1.7 revolutions between laser pulses. In the exemplary embodiment shown the laser beam traveling along laser beam trajectory 50 is focused to a spot size of 138 millimeters with a radiative flux of 7 joules/square centimeter. In the exemplary embodiment illustrated the inert carrier gas is helium and the flow rate of the inert carrier gas 90 and consequently the inert carrier gas with ablated products 95 is 550 cubic centimeters per minute.

The method of standard addition is well known in the art relative amounts of each element can be determined by solving the following equations. The most general form is Equation 1:

$$\left(\frac{m_x + m_s + m_d}{m_x}\right) \times I = k \times \left(\frac{m_s}{m_x} \times C_s\right) + k \times C_x \quad \text{Equation 1}$$

Where I=the instrumental response for the analyte; $m_x$ is the mass of the sample; $m_s$ is the mass of the standard; $C_s$ is the mass fraction of the analyte in the standard; $C_x$ is the mass fraction of the analyte in the sample; k is the instrument sensitivity (response units per unit of mass fraction). The quantity $m_d$ is the mass of the diluent which in the present embodiment is zero because we are not adding a diluent. Thus equation 1 may be rewritten in the form of equation 2:

$$\left(1 + \frac{m_s}{m_x}\right) \times I = k \times \left(\frac{m_s}{m_x} \times C_s\right) + k \times C_x \quad \text{Equation 2}$$

Usually in the method of standard addition the masses of sample and standard are determined during the sample preparation and equation 2 justifies the expectation that the data from an analytical procedure will produce a line of the form:

$$y = a \cdot x + b, \text{ where } a = k \text{ and } b = k \cdot C_x$$

When the data is so plotted the quantity $C_x$ can then be determined by dividing the y-intercept by the slope ($C_x = b/a$). The slope typically being determined by a linear regression of the data points. Therefore, in standard addition analysis, the amount of sample and standard mixed together is a crucial parameter.

In the exemplary embodiment shown the relative masses of the sample and standard will be different depending on the diameter of the ablated circle. The exemplary embodiment used a novel way of determining the respective mass of sample and standard ($m_s/m_x$) ablated using isotope dilution. The multi-element standard is isotopically enriched in Gd (157) at 88 mole % during its preparation, and the same element (Gd) of natural isotopic composition is added to all sample glasses. Knowing the mass fraction and the abundance of Gd in the sample and the multi-element standard the term ($m_s/m_x$) can be calculated using the isotope dilution equation (equation 3).

$$\frac{m_s}{m_x} = \frac{C(Gd)_x}{C(Gd)_s} \times \frac{M_s}{M_x} \times \frac{R_{Gd} \times A_X^2 - A_X^1}{A_S^1 - R \times A_S^2}$$

Equation 3

In equation 3 $C(Gd)_x$=gadolinium mass fraction in the multi-element standard (micrograms/gram); $C(Gd)_s$= gadolinium mass fraction in the sample (micrograms/gram); $M_x$=molar mass of natural gadolinium in the multi-element standard (grams/mole); $M_s$=molar mass of natural gadolinium in the sample (grams/mole); $A_X^1$=Gd isotope abundance of isotope 1 in the sample spiked with natural Gd (%); $A_X^2$=Gd isotope abundance of isotope 2 in the sample spike with natural Gd (%); $A_S^1$=Gd isotope abundance of isotope 1 in the multi-element standard (%); $A_S^2$=Gd isotope abundance of isotope 2 in the multi-element standard (%); $R_{Gd}$=measured isotopic ratio (isotope 1/isotope 2) in the ablated products as measured by ICP-MS. In the exemplary embodiment the mass ratio is determined in real time, and on-line by a point per point data treatment. This makes it possible to access different mass ratios for the same mass spectral analysis. Each mass spectral analysis data point corresponds to a single unique mixing of sample and multi-element standard made with a single laser beam trajectory with the spinning sample cell.

The spinning sample cell for LA-ICP spectrometry illustrated in the exemplary embodiment together with the method of standard addition using isotopically enriched multi-element standards overcomes the limitations of the prior art in that it allows samples to be analyzed even if there are difference in the amount of the sample ablated and the amount of multi-element standard ablated. Such differences may occur due to differences in transparency, matrix, composition, or level position. When differences occur the sample can be analyzed using the spinning cell for LA-ICP-MS because the mass ratio of Gd isotopes indicates the relative amount of sample and standard reaching the ICP-MS.

To calculate an elemental concentration, a linear regression is obtained for each "mixing ablation" (quasi-simultaneous ablation of the sample and standard during the spinning ablation with a single laser beam trajectory 50). The data acquisition consisted in recording 30 seconds of gas blank in order to subtract the background level from each isotope before the ablation. Then, ablation is performed on the sample alone (laser beam trajectory positioned so as to ablate a circle exemplified by element 60 in FIG. 3) and on both sample and standard (laser beam trajectory positioned so as to ablate a circle exemplified by either of elements 63 and 66 in FIG. 3) while the revovable sample holder 10 is spun.

Figure 5:
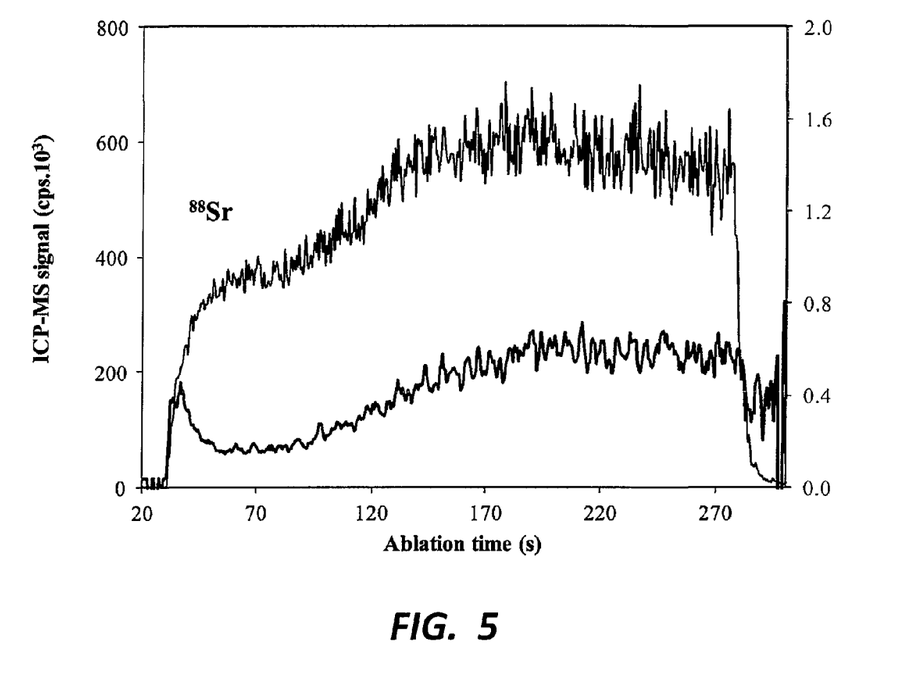
FIG. 5 is a plot illustrating an exemplary mass spectral signal for the isotope Sr(88) and the corresponding calculated ratio: Sr(88) mass in the standard/Sr(88) mass in the sample over a single ablation period.

FIG. 5 is a plot illustrating an exemplary mass spectral signal for the isotope Sr(88) and the corresponding calculated ratio of Sr(88) mass in the standard/Sr(88) mass in the sample over a single ablation period. As it can be seen in FIG. 5, an initial homogenization time is required to obtain a complete mixing of the aerosols. Therefore, the first 30 seconds of ablation are discarded. A selection of the additions is then collected in accordance with the expected concentration. Usually additions are found to vary from 50 mg/kg to 350 mg/kg when using the 250 mg/kg multi-elemental glass standard and 200 mg/kg to 500 mg/kg when using the 500 mg/kg elemental glass standard. These variations depend on the ablation rate, the position of both samples and the location of the ablation. For expected concentration lower than 100 mg/kg, additions from 0 to 200 mg/kg are selected while additions from 200 to 500 mg/kg are chosen for higher expected concentrations.

Figure 6:
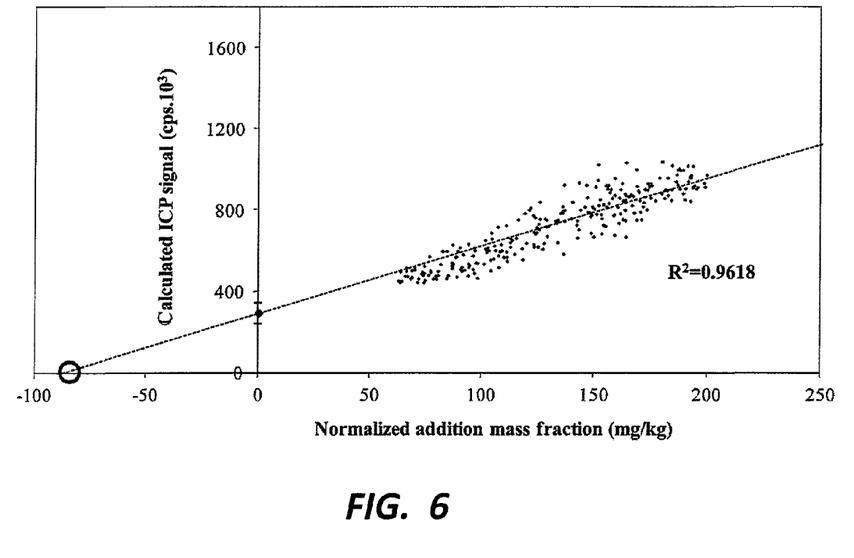
FIG. 6 is a plot of an exemplary set of data illustrating the application of the method of standard addition using the spinning cell for fast standardization and analysis of LA-ICP analysis.

FIG. 6 is a plot of an exemplary set of data illustrating the application of the method of standard addition using the spinning cell for fast standardization and analysis of LA-ICP analysis. Three replicates of the sample alone ablations as illustrated by laser trajectory 60 in FIG. 3. These replicates are considered a "no addition" ablation, and the average is plotted as the y intercept in FIG. 6. Then five replicates of both sample and standard are collected with a range of laser trajectories as illustrated by laser trajectories 63 and 66 in FIG. 3. FIG. 6 illustrates an exemplary plot of data from a single exemplary replication of both sample and standard. The isotopic ratio Gd(57)/Gd(58) is monitored for each ablation replicate in order to know the exact ablation ratio between the sample glass and the multi-elemental glass standard for each ablation. This ratio is corrected for mass bias using the "no addition" ablation of sample alone (which contained natural abundance Gd).

The ICP-MS signal of the three replicates of the sample alone are averaged and used as the "no addition" point for the five linear regressions obtained with the five replicates of the sample and standard "mixing ablation". Each regression line is forced to pass through the "no-addition" point for each sample. Each point of the ICP-MS signals is considered as one addition. This plot shows an exemplary data set for the Sr(88) isotope of the element strontium obtained from the simultaneous analysis of an exemplary embodiment of a glass incorporating the NIST SRM 612 sample as received, and an exemplary embodiment of the 250 milligram/kilogram sample of the multi-element standard in an exemplary embodiment of the spinning sample cell for LA-ICP-MS. After calculation of the linear regression the data gives the mass fraction of strontium as the x intercept.

The data acquisition consisted in recording 30 seconds of gas blank in order to subtract the background level from each isotope before the ablation. Then, ablation is performed on the sample alone (diameter circle below 3 mm) and on both samples (diameter circle above 3 mm) while the sample holder is spun. Three replicates of the sample alone ("no addition" ablation) and five replicates of the mixing are collected with a range of diameter circles less than 13 mm. The isotopic ratio Gd(157)/Gd(158) is monitored in order to know the exact ablation ratio between the sample glass and the multi-elemental glass standard. This ratio is corrected for mass bias using the "no addition" ablation (with natural abundance Gd).

The ICPMS signal of the three replicates of the sample alone are averaged and used as the "no addition" point for the five linear regressions obtained with the five replicates of the "mixing ablation". Each regression line is forced to pass through the "no-addition" point for each sample. Each data point of the ICP-MS signals is considered as one addition.

The spinning cell for LA-ICP spectrometry relies on the fact that the ICP-MS signal from the ablation of one uncut sample alone is not significantly different when using different circle diameters. For the mixing of two materials (one half of standard and one half of sample), replicates consistently for different laser beam trajectories (which produces different ablation tracks with different relative amounts of sample and standard. This change in ablation track does not change the short time period between the ablation of the first and the second half-samples for a given rotation speed when the samples are centered. However, with a larger diameter, the laser will more likely ablate a fresh surface and result in a less deep ablation than with a smaller circle diameter. Therefore, it is important to study the repeatability obtained on a series of ablations spaced by several hundreds of micrometers. For this purpose, an uncut glass bead of SRM 2586 is placed inside the ablation cell and analyzed with circle diameter from 1 mm to 13 mm (which correspond to the diameters used during the quantification of the SRM fused in glass). Although the sample is planar, the focus position is checked before each ablation.

Figure 7:
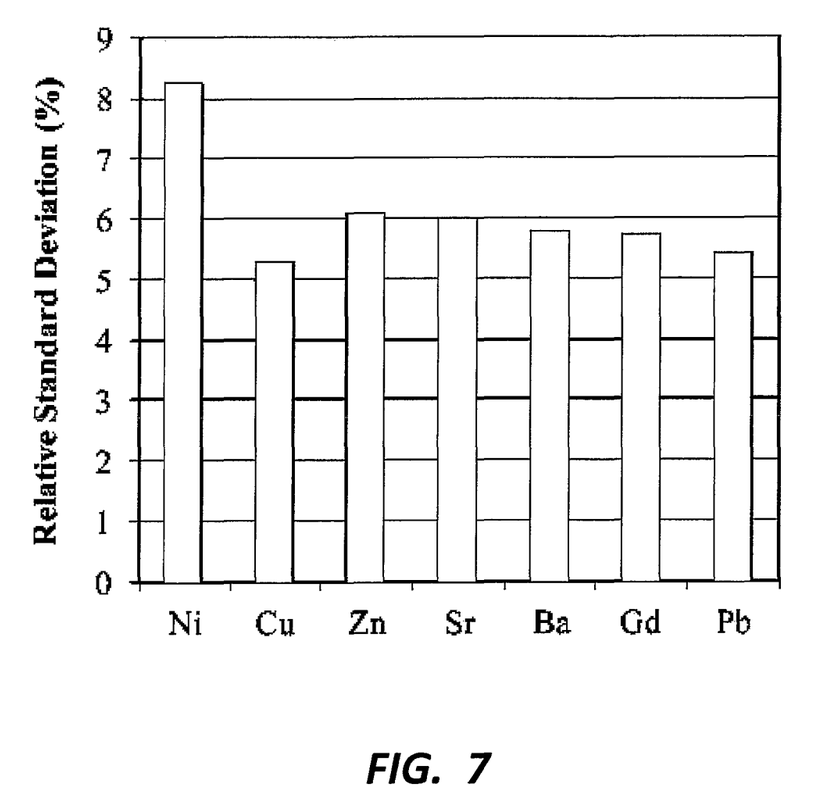
FIG. 7 is a plot of relative standard deviations of ablation analysis results for an exemplary sample using an exemplary embodiment of a spinning sample cell for fast standardization and analysis by LA-ICP spectroscopy.

FIG. 7 is a plot of relative standard deviations of ablation analysis results for an exemplary sample using an exemplary embodiment of a spinning sample cell for fast standardization and analysis by LA-ICP spectroscopy. FIG. 7 illustrates the repeatability of the analytic procedure using an exemplary embodiment of a spinning cell for LA-ICP-MS analysis. FIG. 7 shows the relative standard deviations obtained for the metals nickel, copper, zinc, strontium, barium, gadolinium, and lead analyzed from an exemplary embodiment of the SRM 2586 sample placed in an exemplary embodiment of the spinning cell for LA-ICP-MS analysis. Since These standard deviation values are small, and there no particular trend is observed in the signal intensity of the series of ablation tracks. This means that an ablation track corresponding to a laser beam trajectory within 1.5 mm of the motor axis adequately represents the "no addition point" for linear regression.

Figure 8:
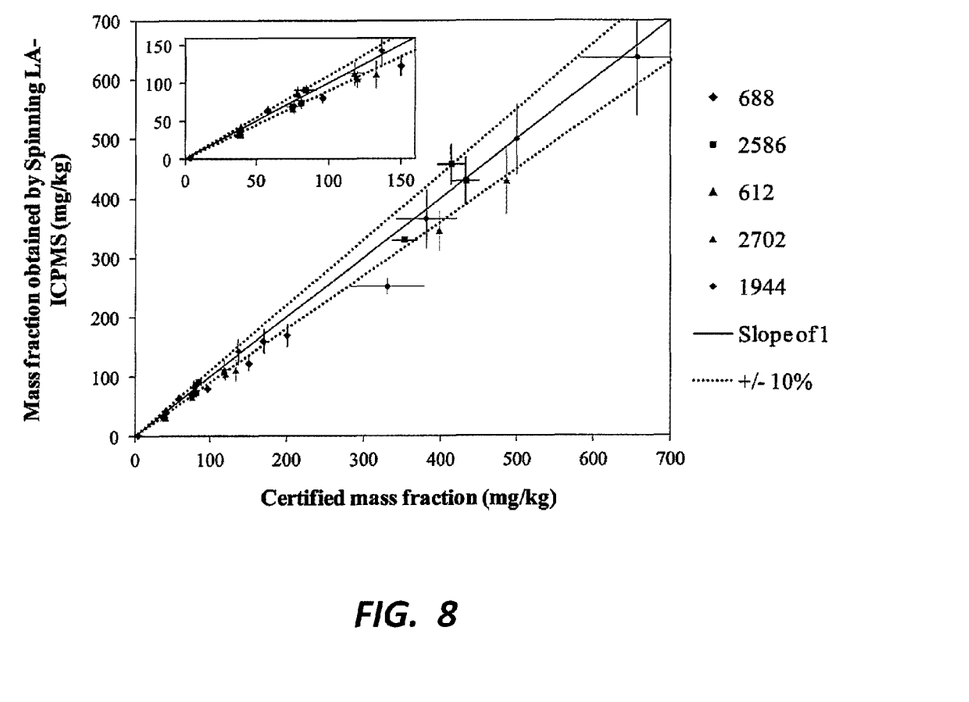
FIG. 8 is an example of a plot obtained to show actual verses observed concentrations for a set samples using spinning cell for LA-ICP spectroscopy.

FIG. 8 is a plot of the actual concentration of an exemplary set of known samples verses the observed concentrations for an exemplary set of samples using an exemplary embodiment of a spinning cell for LA-ICP-MS.

The spinning cell for LA-ICP-MS analysis is used combined with the method of standard addition to analyze four different samples as received for which the concentration of elements is known. These samples are supplied as powder standard reference materials and fused in beads as exemplified in the method shown in FIG. 4. FIG. 8 shows the average error considering all elements and all SRMs is 5.6%.

The average error is found to be below 15% for most of the concentrations obtained except Pb in SRM1944 and Ni and Cu in SRM 688 although these last concentrations are not certified. The average error is below 5% for 10 different concentrations. Accuracies as low as 0.6% for Pb in SRM 2586, and 0.3% for Ba in SRM 1944 are also observed. The relative standard deviation is calculated based on five mixing ablations and found to be in the range of 0.6% to 17% with an average precision of 10%.

Certain elements and SRMs give better results than others. For example concentrations obtained in SRM 2586 for the 6 elements studied showed accuracy in the range of 0.6% to 10.9% with a precision better than 10%. These differences in accuracy could result from small in homogeneities in the sample glass thus affecting the determination of the point with no addition, small interferences, and or additions that are not perfectly adapted to the sample concentration.

The spinning cell for LA-ICP-MS analysis used on SRM 612 is also performed using the multi-elemental glass obtained by Lithium borate fusion. Even though SRM 612 has a different matrix than the standard glass, the average error is 9% considering all elements. This demonstrates that even samples with a matrix different from that of the standard can be analyzed as long as one element is known in the sample and its corresponding isotopically-enriched counterpart has been added to the standard. In the case of SRM 612, the certified concentration of gadolinium (39 mg/kg) is used to determine the ratio $m_s/m_x$ for each element. The repeatability of the ablation of the sample without any addition will account for most of the result uncertainty. The relative standard deviation on the ratio 157Gd/158Gd will also have an influence To demonstrate the potential of this technique, a sample of the Allende meteorite under powdered form was analyzed. The results obtained using Spinning LA-ICPMS are in good agreement with the literature with an average error of 11%. The average precision is 12% which slightly poorer than for SRMs, mainly because the additions are less adapted to this sample with both high and low concentrated elements. For example, the additions were between 300 and 400 mg/kg, thus were too small for Ni which is very concentrated in the meteorite. However, the error on the Ni concentration is 13% which is still reasonably good considering such low additions. For low concentrated elements such Ba and Pb only the lower additions were kept i.e. between 50 (which was the lowest possible addition) and 200 mg/kg.

The spinning cell for LA-ICP spectroscopy makes the method of standard addition more convenient, and less time consuming for chemical analysis. The method of standard addition has many advantages such as reduced matrix effects. The spinning cell for LA-ICP spectroscopy together with the inherent method of its use described herein adds the advantage of sample fusion, such as an improved homogeneity of analytes in the sample compared to pellets, and additional advantage that only one standard is needs to be prepared, and that standard can be reused after polishing. The method inherent in using the spinning cell for LA-ICP spectrometry described herein makes possible multiple standard/sample mixes without opening the ablation chamber. Once the multi-element glass standard is prepared, the whole quantification procedure (fusion, sawing, and replicate ablations of sample alone and sample/standard) can be performed in less than 2 hours. This time may be shortened by using a casting dish already in a suitable form for the glass to avoid the sawing step. The fusion step can be automated and be performed on several samples at the same time with recent instrumentation. Compared to external calibration, time is spared because there is no need to establish a calibration curve with standards that are scarce and difficult to match with samples in terms of matrix. The accuracy of the methodology on selected elements is similar and sometimes better than regular matrix-matched external calibration using samples fused with lithium borate. It is however better than external calibrations involving the preparation of pellets of powders with the use of binder.

What is claimed is:

1. A dual matrix LA-ICP spectroscopic analysis system specifically adapted for performing a method of dual matrix LA-ICP analysis comprised of:
   at least one ablation chamber housing which substantially encloses an ablation chamber;
   an inductively coupled plasma ionization chamber fluidly connected to said ablation chamber;
   wherein said ablation chamber housing is adapted for passage of a laser beam though the inner and outer surfaces of said ablation chamber housing;
   wherein said ablation chamber housing includes at least two apertures to enable the entry and exit of an inert carrier gas into said inductively coupled plasma ionization chamber fluidly connected with said ablation chamber housing;
   a revolvable sample receptacle adapted to secure a quantity of ablative material, wherein revolvable sample receptacle includes a designated area for a quantity of a sample under test and a designated area for a standard sample;
   a motor operatively coupled to said revolvable sample receptacle and able to cause said sample receptacle to spin around an axis to produce a spinning sample under test; and wherein
   a laser component which produces a laser beam, wherein said laser beam is directed at said spinning sample under test and wherein said laser can be configured to produce a static ablation trajectory that is in contact with said ablative material held within said spinning sample chamber for an ablation period.

2. The apparatus of claim 1 wherein said laser beam may be configured to selectively ablate only said sample under test during said ablation period.

3. The apparatus of claim 1 wherein said sample under test and said standard sample and said laser beam may configured to concurrently ablate said sample under test or said standard sample to produce said plurality of ablation products during said ablation period.

4. The apparatus of claim 1 which further includes a plurality of variably positioned trajectory settings, and wherein said laser and said sample under test is selectively positioned with respect to each other by a user.

5. The apparatus of claim 1 which further includes an analyte sensor wherein said plurality of ablation products include analyte sensor.

6. The apparatus of claim 1 which further includes a quantity of a sample under test having an unknown composition wherein said sample is comprised of ablative material.

7. The apparatus of claim 1 wherein said ablation chamber is connected to an inductively coupled plasma ionization chamber.

8. The apparatus of claim 1 wherein said inductively coupled plasma ionization chamber is operatively coupled to a mass spectrometer.

9. The apparatus of claim 1 wherein sample under test and said standard sample include a substantially similar matrix.

10. The apparatus of claim 1 wherein said substantially similar matrix that includes materials selected from a group consisting of: a glass, a known quantity of an isotopically enriched element, a known quantity of a rare earth element.

11. The apparatus of claim 1 wherein the ratio of flow rate to chamber volume is less than two times the rate of repetition of the application of the laser pulse.

12. The apparatus of claim 1 wherein said standard sample is a multi-element standard.

13. The apparatus of claim 1 wherein said chamber is constructed from polymethylmethacrylate.

14. A method for performing LA-ICP spectroscopic analysis specifically utilizing a dual matrix spinning sample apparatus which includes the steps of:
   dispersing a known quantity of material in a first solid matrix to create a sample under test;
   preparing a standard sample by dispersing a known amount of a material of known composition in a second solid matrix that is substantially similar to said first solid matrix;
   placing said sample under test and said standard sample in a spinning sample holder of a dual matrix spinning sample apparatus;
   selectively ablating said sample under test and said standard sample while said sample holder is spinning with a laser to produce a quantity of ablation products including analytes; and
   transporting said ablation products to said inductively coupled plasma ionization chamber; and
   measuring said analytes analyzing the ions generated by said inductively coupled plasma ionization chamber by an analytical technique compatible with inductively coupled plasma ionization.

15. The method of claim 14 which further includes the step of reusing a standard sample for multiple ablation periods.

16. The method claim 14 which further includes the step of repeating the step of selectively ablating said sample under test and said standard sample while said sample holder is spinning with a laser to produce a quantity of ablation products including analytes for multiple ablation periods.

17. The method of claim 14 which further includes the step of adjusting the trajectory of said laser with respect to the position of said sample under test after each successive ablation period.

18. The method of claim 14 which further includes the step of successively adding a known quantity of analyte to said ablation products of said sample under test within said ablation chamber to compensate for matrix effects.

* * * * *